United States Patent [19]
Gimbel

[11] Patent Number: 5,423,090
[45] Date of Patent: * Jun. 13, 1995

[54] GLOVE WITH FLOATING PUNCTURE RESISTANT PAD

[76] Inventor: Neal I. Gimbel, 5815 N. 25th St., Phoenix, Ariz. 85016

[*] Notice: The portion of the term of this patent subsequent to Nov. 9, 2010 has been disclaimed.

[21] Appl. No.: 147,135
[22] Filed: Nov. 3, 1993
[51] Int. Cl.6 .................................... A41D 19/00
[52] U.S. Cl. ............................. 2/161.7; 2/163; 2/168
[58] Field of Search ............... 2/21, 163, 16, 159, 2/161.6, 161.7, 164, 167, 168, 169, 901

[56] References Cited

U.S. PATENT DOCUMENTS

| | | | |
|---|---|---|---|
| 3,633,216 | 1/1972 | Schonholtz | 2/168 |
| 4,858,245 | 8/1989 | Sullivan et al. | 2/21 |
| 4,864,661 | 9/1989 | Gimbel | 2/167 |
| 4,901,372 | 2/1990 | Pierce | 2/167 |
| 4,995,119 | 2/1991 | Codkind | 2/163 |
| 5,070,543 | 12/1991 | Beck | 2/163 |
| 5,259,069 | 11/1993 | Gimbel | 2/163 |

Primary Examiner—Clifford D. Crowder
Assistant Examiner—Amy Brooke Vanatta
Attorney, Agent, or Firm—Tod R. Nissle

[57] ABSTRACT

A puncture resistant surgical glove. The glove includes a puncture resistant pad which is positioned on one of the fingers of the glove. A finger stall is pulled over the glove finger and the puncture resistant pad and is sealed on the glove by dipping the glove in a latex bath. The thickness of the material comprising the finger stall is less than thirty thousandths of an inch.

6 Claims, 1 Drawing Sheet

GLOVE WITH FLOATING PUNCTURE RESISTANT PAD

This invention relates to gloves.

More particularly, the invention relates to a hand conforming elastic surgical glove which is puncture resistant at certain selected areas on the glove and therefore reduces the likelihood that surgeons and other medical personnel will contract AIDS, hepatitis and other diseases while performing surgery, drawing blood, or otherwise administering to the needs of patients.

In another respect, the invention relates to a puncture resistant surgical glove which utilizes a pliable woven material layer on an elastic foundation glove without requiring that the woven material be fastened to the foundation glove with adhesive or other means.

In a further respect, the invention relates to a puncture resistant surgical glove of the type described in which water or other fluids are prevented from penetrating the pliable woven material without requiring that the pliability of the woven material be sacrificed by impregnating the woven material with a water repellant material or by fastening the woven material to an adjacent layer of water resistant material.

Various types of puncture resistant surgical gloves are well known in the art. See for example, U.S. Pat. Nos. 4,864,661 to Gimbel and 4,742,578 to Seid. These patents endeavor to improve the puncture resistance of conventional latex gloves without unduly sacrificing the pliability and thinness of latex gloves. A problem encountered in producing puncture resistant gloves is that it difficult to obtain material which is thin, elastic, water proof, and puncture resistant. While latex and other rubber materials are thin, elastic and water repellant, they do not exhibit a high degree of puncture resistance. While woven materials comprised of nylon or other polymer yarns can exhibit a high degree of puncture resistance, they are not, standing alone, water resistant, they must be fastened to a foundation glove with adhesive or other material which increases the cost of manufacture of the glove and adversely affects the pliability of the woven material and of the resulting surgical glove, and they are not elastic. The tendency of woven materials to absorb blood or other body fluid is a particular problem because health care personnel wish to avoid the maintenance of such fluids in gloves positioned immediately adjacent the surface of their hands.

Accordingly, it would be highly desirable to provide a puncture resistant surgical glove which could utilize an elastic thin rubber foundation glove which would readily conform to a surgeon's hands and which could also utilize a puncture resistant woven material without exposing the woven material to bodily fluids and without requiring that the woven material be fastened to the foundation glove with adhesive or be impregnated or laminated with a water repellant chemical or material.

Therefore, it is a principal object of the invention to provide an improved surgical glove.

A further object of the invention is to provide an improved surgical glove which utilizes a foundation glove fabricated from a thin, elastic, waterproof material and utilizes a puncture resistant woven or other material which floats with respect to and can slide over the foundation glove.

Another object of the invention is to provide an improved surgical glove of the type described which, without laminating or impregnating the puncture resistant woven material with another material, prevents bodily fluids from contacting the woven material during use of the glove.

Still a further object of the invention is to provide an improved surgical glove of the type described in which the position and orientation of the puncture resistant woven material in the glove is secured by expansion of the glove which occurs when the glove is placed on the hand of a surgeon or other health care personnel.

These and other, further and more specific objects and advantages of the invention will be apparent to those skilled in the art from the following detailed description thereof, taken in conjunction with the drawings, in which.

Briefly, in accordance with my invention, I provide an improved puncture resistant surgical glove. The glove includes a foundation glove, an intermediate layer of puncture resistant material positioned adjacent the foundation glove, and, an outer layer. The foundation glove is composed of a thin, resilient elastic rubber and includes a front surface; a rear surface; and, a plurality of stalls each for one of the digits of a hand. The front surface of each of the stalls is positioned over the volar or inner surface of one of the digits when the glove is worn. The rear surface of each of the stalls is positioned over the dorsal or outer surface of one of the digits when the glove is worn. The intermediate layer is positioned over and contacts the front surface of one of the stalls. The outer layer is composed of a thin, resilient elastic rubber overlaying and contacting the intermediate layer of material. The outer layer resiliently expands when the glove is worn and presses the intermediate layer of material against the foundation glove and one of the digits of the hand such that the intermediate layer frictionally engages the foundation glove and the outer layer, and such that the frictional engagement of the intermediate layer with the foundation glove and the outer layer helps prevent the intermediate layer from moving with respect to the foundation glove and the outer layer. The intermediate layer is not fastened to the outer layer or to the foundation glove.

Figure 1:
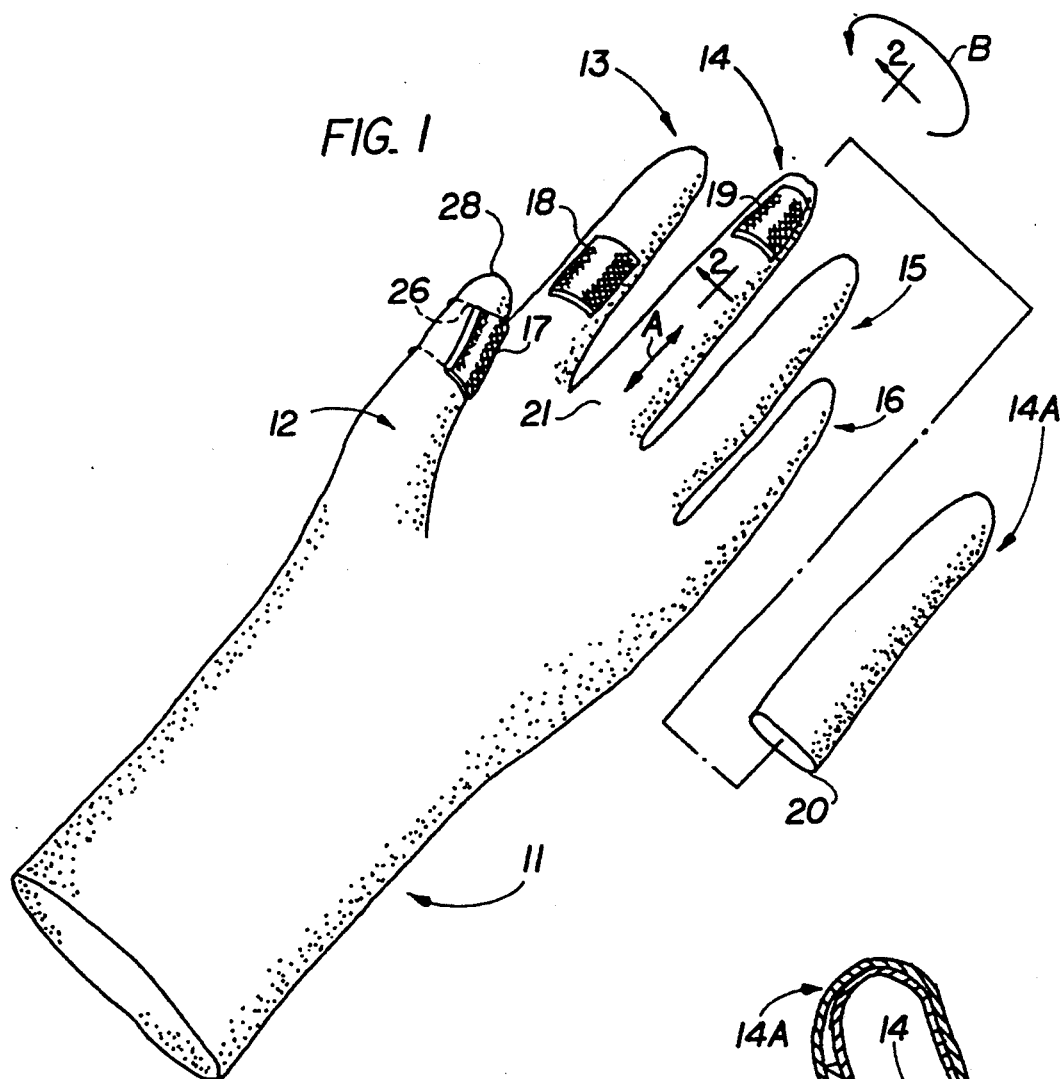
FIG. 1 is a perspective view illustrating a surgical glove constructed in accordance with the principles of the invention.
Figure 3:
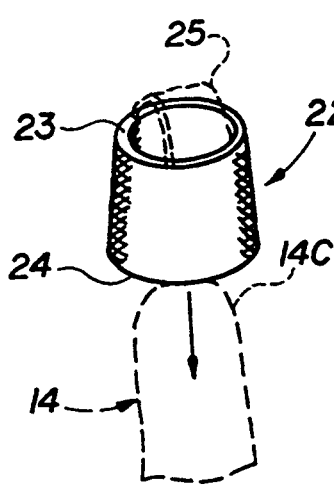

Turning now to the drawings, which depict the presently preferred embodiments of the invention for the purpose of illustrating the practice thereof and not by way of limitation of the scope of the invention and in which like characters represent corresponding elements throughout the several views, FIG. 1 illustrates a surgical glove generally identified by reference character 11 and including elongate stalls 12 to 16 for the thumb and finger digits of a surgeon's hand. In FIG. 1, the front surface of the glove is visible and would cover the inner wrist, palm and inner finger surfaces of the hand. The back surface of the glove is not visible and covers the back of the wrist and back of the hand and fingers. Stalls 12 to 14 include puncture resistant portions 17 to 19 positioned on but not fastened to stalls 12 to 14, respectively. When glove 11 is worn by a surgeon, portions 17 to 19 preferably remain positioned over a segment of a finger spaced away from the joints of the finger so as not to interfere with the bending of the joint of the finger. If, however, a puncture resistant portion 17 to 19 is thin and pliable, it can be positioned over the joint of a finger. If desired, an elastic band 26 can be attached to a portion 17 to maintain portion 17 in position on a stall 12. Band 26 extends from one edge of portion 17, around the back surface of stall 12, and to the other edge of portion 17, i.e., band 26 and portion 17 collectively completely circumscribe stall 12. In FIG. 3, portion 22 also completely circumscribes a stall 14.

The size of band 26 and portion 17 can be increased such that band 26 covers the back area of stall 12 shown in FIG. 1 and also extends upwardly over the back surface of stall 12 up to tip 28 of stall 12 and such that portion 17 covers the front surface of stall 12 shown in FIG. 1 and also extends upwardly over the front surface of stall 12 to tip 28. In this embodiment, band 26 and portion 17 meet at tip 28.

Although a puncture resistant portion can be fabricated from any desired woven or non-woven material, a woven material is presently preferred in the invention because woven materials are, in comparison to many polymers, more readily made supple and puncture resistant. One example of a material for portions 17 to 19 is obtainable from Burlington Industries, 1345 Avenue of the Americas, N.Y., N.Y. 10019, and has the specification listed below:

Material: High-density interwoven nylon yarn
Style No.: 55116
Weight: 1.5 ounces per square yard
Thickness: Approximately three-thousands (3/1000) of an inch
Type of Weave: Plain
Warp: 30 denier nylon yarn, dupont type 285, zero twist. 240 yarns per inch 26 filaments per yarn
Fill: 20 denier nylon yarn, DuPont type 285, zero twist 200 yarns per inch 7 filaments per yarn
Color: White The Burlington Industries material described above has a resistance to penetration by a needle which is three to five time greater than the resistance of latex rubber of the same thickness. In the practice of the invention, it is, however presently preferred that such cloth be doubled or tripled over so that the thickness is at least six one thousands of an inch, preferably at least nine one thousands of an inch. A single layer of such cloth typically is not, in the practice of the invention, sufficient to give an acceptable protection against penetration by a sharp needle. Portion 19 could also, for example, comprise a woven fiberglass fabric, called S-2 glass, produced by Owens-Corning Fiberglass Corporation, can comprise a clear polymer like the "BG" bag produced by Cryovac, comprise a weave made from fibers fabricated from DuPont's Kevlar aramid, or comprise a weave made from Kevlar fibers and other fibers used in combination with the Kevlar fibers. Cryovac is a division of W. R. Grace, Company. The BG bag is noted on page 127 of the May 1987 issue of *Packaging Magazine*.

The above described Burlington Industries material is essentially non-elastic. If desired, elastic puncture resistant materials can be utilized instead of non-elastic materials.

Further examples of materials which can, if they have greater puncture resistance than conventional latex surgical glove, be utilized in fabricating a portion 19 of the glove of the invention are found in the October 1986 volume of Scientific American in articles beginning on pps. 50, 58, 66, 92, 102, 118, 126, 146, 158, 168, 178, and 182.

Portion 19 can comprise a single crystal of aluminum oxide, a thin coating of aluminum, steel, silver, or other metals. Strands used to weave a portion 19 can be formed from metals, ceramics, polymers, composites, and other puncture resistant materials.

After a woven puncture resistant portion 19 is positioned on the front surface of a stall 14 in the manner illustrated in FIG. 1, it is necessary to maintain portion 19 in position adjacent stall 14. This is not accomplished by using adhesive or other means to fasten portion 19 in fixed position on stall 14. Instead, a stall 14A is slide over stall 14 and the open end 20 of stall 14A is glued to the lower open end 21 of stall 14 to seal portion 19 in position on stall 14. Once stall 14A is sealed on stall 14, water cannot (unless stall 14 is cut or punctured) penetrate intermediate stalls 14A and 14 and be absorbed by woven portion 19. In another embodiment of the invention, once stall 14A is pulled over stall 14, the entire glove 11 is dipped in a bath of liquid latex. The latex in the bath coats the entire glove 11 and seals the open end 20 of stall 14A to the lower portion 21 of stall 14. When glove 11 is dipped in a bath of liquid latex, it is critical that the thickness of the material at open end be as thin as possible so that a thin layer 30 of latex from the liquid bath will effectively seal end 20 to portion 21. The thickness of end 20 is less than thirty one-thousandths of an inch and greater than one ten-thousandth (0.0001) of an inch, and preferably is less than five one-thousandths (0.005) of an inch. The size and shape of end 20 closely fits around and conforms to portion 21 so that parts of end 20 will not wrinkle when end 20 is sealed to portion 21. End 20 closely fits portion 21 so that end 20 extends smoothly around portion 21 and parts of end 20 cannot overlap. The inner diameter of end 20 closely approximates the outer diameter of portion 21. If, for example, end 20 is too large, then a part of end 20 typically must be folded over itself so that end 20 snugly fits around portion 21. Folding a part of end 20 over itself is highly undesirable and increases the difficulty of sealing end 20 to portion 21 by dipping the glove in a bath of liquid latex. Both of stalls 14 and 14A are elastic so both stalls can simultaneously expand and contract when the glove is worn on the hand of a physician or other person. Fabricating stall 14A from a non-elastic material is not preferred the practice of the invention.

After the glove is withdrawn from the latex bath, the glove is heated to cure and dry the liquid latex. Portion 19 frictionally engages stalls 14, 14A and tends to maintain a fixed position with respect to stalls 14, 14A. Portion 19 need not be attached or fastened to either stall 14 or 14A and can float between stalls 14 and 14A by sliding in the direction of arrows A in FIG. 1, or, by sliding circumferentially around stall 14 and the longitudinal axis of stalls 14, 14A in the directions indicated by arrows B.

Figure 2:
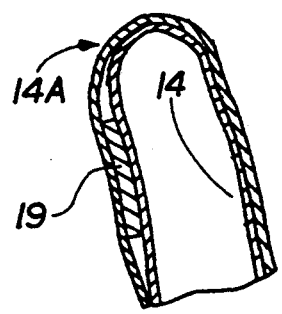
FIG. 2 is a section view of a stall of the glove of FIG. 1 taken along section line 2—2 thereof and illustrating further construction details thereof; and, FIG. 3 is a perspective view illustrating an alternate configuration of a woven material which can be utilized in the practice of the invention.

FIG. 2 illustrates portion 19 in position between stalls 14 and 14A. Portion 19 preferably is not, but can be, glued or otherwise fastened to stalls 14, 14A. Stalls 14, 14A are, but need not be, preferably rubber or some rubber composition, and portion 19 frictionally engages stalls 14, 14A such that portion 19 tends to maintain the position between stalls 14, 14A shown in FIG. 2. Further, when the latex glove illustrated in FIGS. 1 and 2 is worn, stalls 14 and 14A stretch to conform to the fingers of a surgeon's hand. When stall 14A stretches and expands in size, stall 14A presses portion 19 against stall 14 and against the digit in stall 14. Such compression of portion 19 against stall 14 help maintain portion 19 in fixed position with respect to stalls 14 and 14A.

In the embodiment of the invention shown in FIG. 3, a puncture resistant woven portion 22 is fabricated in a conical form which slips in position over a stall 14. The diameter of the upper circular opening 23 of pliable portion 22 is sized to fit over the tip of a finger but not to fit over the knuckle of the finger. Similarly, opening 24, which has a larger diameter than opening 23, will not fit over the knuckle of the finger. Accordingly, portion 22 is sized to maintain its position on stall 14 covering the outer joints of a finger, i.e., over the joint at the tip of the finger and the intermediate joint of the finger. Portion 22 can be sized so it will slide over and cover only the joint comprising the tip of the finger, will slide over and cover all joints of the finger, etc. A loop, indicated by dashed line 25 in FIG. 3, can be attached to opening 23. The loop extends from one side of opening 23 to the other end of opening 23. Loop 25 prevents portion 22 from sliding to far down stall 14 because the outer or distal tip 14C of stall 14 contacts loop 25.

Not having to fasten a portion 19 to a stall 14 with adhesive or other material reduces the cost of manufacture of the glove. Equally important, when portion 19 comprises woven material, portion 19 is not exposed to bodily fluids. Further, the method of the invention obviates having to impregnate a woven portion 19 with a water repellant material or having to use heat or adhesive to attach a laminate layer to portion 19 to render portion 19 water repellant.

In one method of producing gloves in accordance with the invention, a conventional aluminum, ceramic or other mold in the shape of a human hand with fingers extended is produced. The palm, finger, etc. surface of the mold are generally smooth and do not reflect the skin wrinkles, fingernails, etc. found on an actual human hand. The mold is dipped in a latex bath. After the mold is removed from the bath, the latex on the mold is allowed to dry to form a foundation glove. A puncture resistant portion 19 is placed in a selected position on the front surface of stall 14 of the foundation glove. Portion 19 preferably is not glued or otherwise fastened or permanently attached to stall 14. An elastic band similar to band 26 (FIG. 1) can be attached to portion 19 to secure portion 19 in position around stall 14 and around the portion of the mold covered by stall 14. The amount by which the elastic band stretches when placed over stall 14 preferably is minimal so that after the glove is removed from the mold the band does not, when it resiliently contracts to its normal configuration, collapse the stall.

Once a portion 19 is positioned on stall 14, a stall 14A is pulled over the puncture resistant portion 19 and over the stall 14 such that the bottom of stall 14A is adjacent, contacts, and circumscribes the bottom 21 of stall 14. Stall 14A is presently preferably made from latex, but can be made from a plastic which shrinks when subjected to heat or can be made from any other desired material. The mold is then dipped in the latex bath a second time to coat stall 14A and to coat the portions of the foundation glove which are not covered by stall 14A. The second coat of latex seals the bottom 20 of stall 14A to the bottom 21 of stall 14 so that water and bodily fluids cannot penetrate intermediate stalls 14 and 14A. Portion 19 is not fastened to stalls 14, 14A and is free to float or work its way along stall 14 in the direction of arrows A or around stall 14 in the direction of arrows B. As used here, a portion 19 is deemed to float intermediate stalls 14, 14A if portion 19 can slide or work its way around stall 14 in at least one direction of travel. If, for example, in FIG. 1 portion 19 can (after stall 14A is slid over stall 14 and the bottom 20 of stall 14A is sealed to the bottom 21 of stall 14) slide intermediate stalls 14, 14A in a direction of travel away from the tip of stall 14 and toward the bottom of the glove 11, then portion 19 can slide in at least one direction of travel. When a portion 17 is provided with an elastic retaining band 26, the portion 17 can be slid or worked along at least a portion of the length of stall 12 and therefore floats on stall 12. A portion 17, 18, 19 can include one or more layers of material; each such layer may or may not be impregnated with a chemical composition or be attached to any adjacent layers in the portion 17, 18, 19.

After the second layer of latex dries, the glove is peeled off of the mold and is ready for use. Portion 19 floats intermediate stalls 14, 14A.

In use, the glove is pulled onto the hand of a surgeon. The glove is preferably, but not necessarily, sized such that the foundation glove and stall 14A must stretch and resiliently expand to conform to the surgeon's hand. When the glove expands, stalls 14 and 14A expand such that stall 14A generates a compressive force against portion 19. The compressive force presses portion 19 against stall 14 and the digit housed by stall 14. The compressive force against portion 19 increased the magnitude of the frictional forces between portion 19 and stalls 14, 14A. These frictional forces function to maintain portion 19 in a fixed position between stalls 14, 14A.

As used herein, the term "puncture resistant material" includes any material having a puncture resistance greater than the puncture resistance of a conventional latex surgical glove commonly utilized by surgeons.

Having described my invention in such terms as to enable those skilled in the art to practice and understand it, and having described the presently preferred embodiments thereof,

I claim:

1. A puncture resistant surgical glove comprising in combination:
   (a) a foundation glove composed of thin, resilient elastic material having
      (i) a lower hand covering portion,
      (ii) a plurality of stalls connected to said covering portion and each for one of the digits of a hand and having a front surface and a rear surface, the front surface of each of said stalls being positioned over the volar surface of one of the digits when the glove is worn, the rear surface of each of said stalls being positioned over the dorsal surface of one of the digits when the glove is worn;
   (b) at least one intermediate layer of puncture resistant material positioned over and contacting at least said front surface of one of said stalls;
   (c) a stall cover composed of a thin, resilient elastic material overlaying and contacting said intermediate layer of material and substantially extending over and covering said one of said stalls, said stall cover having an open end circumscribing said one of said stalls and having a closed end, said resilient elastic material at said open end of said stall cover having a thickness of less than thirty thousandths of an inch; and, (d) at least one outer coating of thin resilient elastic material formed by dipping said foundation glove and stall cover in a liquid bath of said resilient elastic material, said coating
   (i) continuously overlaying and adhering to said stall cover and to at least a portion of said lower hand covering portion, and
   (ii) sealing said open end of said stall cover to said one of said stalls to seal said intermediate layer inside said stall cover between said stall cover and said one of said stalls.

2. The surgical glove of claim 1 wherein
(a) said one of said stalls includes a lower end connected to said lower hand covering portion;
(b) said open end of said stall cover fits over and closely conforms to said lower end of said one of said stalls such that said open end is prevented from wrinkling or folding when said open end is pulled over said lower end of said one of said stalls.

3. A method for manufacturing a puncture resistant surgical glove comprising the steps of:
(a) providing a foundation glove composed of thin, resilient elastic material having
   (i) a lower hand covering portion,
   (ii) a plurality of stalls connected to said covering portion and each for one of the digits of a hand and having a front surface and a rear surface, the front surface of each of said stalls being positioned over the volar surface of one of the digits when the glove is worn, the rear surface of each of said stalls being positioned over the dorsal surface of one of the digits when the glove is worn;
(b) providing a layer of puncture resistant material;
(c) placing said layer of puncture resistant material against said front surface of one of said stalls;
(d) providing a stall cover composed of a thin, resilient elastic material, said stall cover having an open end and having a closed end, said resilient elastic material at said open end having a thickness of less than thirty thousandths of an inch;
(e) drawing said stall cover over one of said stalls such that said open end circumscribes said one of said stalls; and,
(f) dipping said foundation glove and stall cover in a liquid bath of said resilient elastic material to form a coating over said stall cover, said coating
   (i) continuously overlaying and adhering to said stall cover and to at least a portion of said lower hand covering portion, and
   (ii) sealing said open end of said stall cover to said one of said stalls to seal said intermediate layer inside said stall cover between said stall cover and said one of said stalls.

4. The method of claim 3 wherein
in step (a), said stalls of said foundation glove each include a lower end attached to said lower hand covering portion;
in step (d), said open end of said stall cover closely approximates the size of said lower end of said one of said stalls such that said open end conforms to said lower end of said one of said stalls and is prevented from wrinkling or folding when said open end is pulled over said lower end of said one of said stalls; and,
in step (e), said open end is pulled over said lower end of said one of said stalls.

5. The method of claim 4 wherein in step (a), said resilient elastic material is latex; and, in step (f), said resilient elastic material is latex.

6. The method of claim 5 wherein in step (d), said resilient elastic material is latex.

* * * * *